US00PP13163P2

(12) United States Plant Patent
Trees

(10) Patent No.: US PP13,163 P2
(45) Date of Patent: Nov. 5, 2002

(54) ANTIRRHINUM PLANT NAMED 'BALUMYELL'

(75) Inventor: Scott C. Trees, Shell Beach, CA (US)

(73) Assignee: Ball FloraPlant, a division of Ball Horticultural Corporation, West Chicago, IL (US)

( * ) Notice: Subject to any disclaimer, the term of this patent is extended or adjusted under 35 U.S.C. 154(b) by 0 days.

(21) Appl. No.: 09/808,089

(22) Filed: Mar. 14, 2001

(51) Int. Cl.[7] ..... A01H 5/00
(52) U.S. Cl. ..... Plt./322
(58) Field of Search ..... Plt./322

*Primary Examiner*—Bruce R. Campell
*Assistant Examiner*—June Hwu
(74) *Attorney, Agent, or Firm*—Wood, Philips, Katz, Clark & Mortimer

(57) ABSTRACT

A new and distinct Antirrhinum plant named Balumyell is provided. This new cultivar is characterized by its trailing habit and bright yellow flowers.

2 Drawing Sheets

LATIN NAME OF THE GENUS AND SPECIES OF PLANT CLAIMED

Antirrhinum majus.

VARIETY DENOMINATION

Balumyell.

BACKGROUND OF INVENTION

The present invention comprises a new and distinct Antirrhinum plant, hereinafter referred to by the cultivar name Balumyell. This new cultivar was developed by the inventor through a controlled breeding program during August 1997 at Arroyo Grande, Calif. The objective of the breeding program was the development of Antirrhinum cultivars with trailing mounded habit, continuous flowering, excellent basal branching and small, dark green foliage.

Balumyell resulted from the self fertilization of the proprietary Antirrhinum plant designated 90-12 which is characterized by its trailing habit, lavender flowers with orange throat and medium green glabrous foliage. The resulting seed was collected and germinated. From the flowering progeny, a plant was selected in April 1998 and initially designated 560-3.

Asexual reproduction of the new cultivar by terminal or stem cuttings taken during 1998 and 1999 at Arroyo Grande, Calif., U.S.A. has demonstrated that the characteristics of the new cultivar as herein described are firmly fixed and retained through successive generations of such asexual propagation.

SUMMARY OF INVENTION

It was found that the cultivar of the present invention:

(a) exhibits a trailing habit, (b) forms abundant bright yellow flowers and (c) exhibits dark green foliage.

When the new cultivar of the present invention is compared to Chandelier Lemon Blush (Not patented in the United States) it is found that the new cultivar exhibits a somewhat less trailing habit, leaves of a different shape and flowers that are larger, differ in color and are non fragrant as detailed in Table 1.

BRIEF DESCRIPTION OF THE PHOTOGRAPHS

The accompanying photographs show as nearly true as it is reasonably possible to make the same in color illustrations of this type, typical flower and foliage charateristics of the new cultivar.

The first photograph comprises a view of the growth habit of Balumyell with three plants in one pot.

The second photograph comprises a close-up view of flowers and leaves of Balumyell. Size and shape of both flowers and leaves are accurate but colors appear darker than the actual colors. The plants were grown in a greenhouse at West Chicago, Ill., USA.

DETAILED BOTANICAL DESCRIPTION

The Balumyell cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Sep. 26, 2000 in West Chicago, Ill. The readings were taken between 11:00 and 11:45 p.m. under natural light conditions. The plants were produced from cuttings taken from stock plants and were grown for ten (10) weeks in a double poly carbonate covered greenhouse under conditions comparable to those used in commercial practice while utilizing a soilless growth medium and maintaining temperatures of approximately 72° F. during the day and approximately 65° F. during the night.

Classification:

*Botanical.*—*Antirrhinum majus* cultivar Balumyell.

*Commercial.*—Trailing Snapdragon.

Propagation:

*Type cutting.*—Terminal tip.

*Time to initiate roots.*—Approximately 10–14 days with the shorter times generally being experienced in the summer and the longer times in the winter.

*Root description.*—Fibrous, branching.

Plant description:

*General appearance and form.*—Mounded and trailing.

*Plant length (from top of plant to lower flowers).*—Approximately 17.6 cm.

*Plant width.*—Approximately 29.8 cm.

*Branching habit.*—Freely branching. Pinching encourages branching.

*Stem.*—Diameter at lowest node approximately 2 mm, closest to 146D in color, covered with very short, stiff hairs.

*Internode length.*—Approximately 1.4 cm.

Foliage description:

*Shape.*—Narrow elliptic, obtuse apex, attenuate base, entire margin.

*Arrangement.*—Opposite.

*Venation pattern.*—Arcuate.

*Texture.*—Upper and lower surface moderately covered with very short stiff hairs.

*Color of mature foliage.*—Upper surface closest to 137A with venation of 137C, lower surface closest to 137C with venation of 137C.

*Size of mature leaves.*—Approximately 3.2 cm in length; approximately 1.3 cm in width.

*Petiole.*—Length is approximately 4 mm, diameter is approximately 1 mm, color is 137C, surface is moderately covered with very short soft hairs.

Flower description:

*Flowering habit.*—Balumyell is freely flowering under outdoor growing conditions with substantially continuous blooming from spring until fall.

*Flower arrangement.*—Terminal raceme.

*Peduncle.*—Length is approximately 7 mm, diameter is approximately 1 mm, color is closest to 144B.

*Flower.*—Approximately 3.2 cm in length, bilabiate. Lip texture Smooth, margin entire and somewhat undulating. Upper lip is 2 parted, approximately 1.3 cm long, approximately 1.8 cm wide, 3C at edge, 3D at base with venation of 72C. Lower lip is 3 parted, approximately 1.5 cm long, approximately 2.2 cm wide, 3C with area of 9A where lip meets palate. Lower palate is 155D with hairs of 155D along outer edges and hairs of 4A in center, inside throat is 155D with two spots of 4A at base, some hairs of 155D and a few hairs of 4A.

*Flower bud.*—Length is approximately 1.5 cm, width is approximately 8 mm, texture is pilose, color 3D.

*Calyx.*—5 sepals, overlapping at base, approximately 8 mm in length, approximately 3 mm in width, ovate with acute apex, upper and lower surface pubescent, upper and lower surface color is between 137B and 146B in color.

*Reproductive organs.*—Androecium: 4 stamens, 155D in color, 2 are 1 cm in length and 2 are 1.6 cm in length. Anther length is approximately 2.3 mm, color is 164D. Pollen color is closest to 11A. Gynoecium: One pistil. Stigma length is approximately 1.3 mm, color is 145A, style is approximately 1.4 cm long, 145B in color. Ovary is 2 mm in diameter, 145A and covered with short hairs of 155D.

Seed production: Seed production has not been observed.

Disease resistance: Resistance to pathogens has not been observed.

TABLE 1

| CHARACTERISTIC | BALUMYELL | CHANDELIER LEMON BLUSH |
|---|---|---|
| PLANT LENGTH; TOP OF PLANT PLANE TO LOWEST FLOWERS | 17.6 CM | 24.8 CM |
| MATURE LEAF LENGTH × WIDTH | 3.2 CM × 1.3 CM | 2 CM × 1.1 CM |
| FRAGRANCE OF FLOWERS | ABSENT | SWEET |
| FLOWER-WIDTH OF LOWER LIP | 2.2 CM | 1.5 CM |
| FLOWER LENGTH | 3.2 CM | 3 CM |
| FLOWER COLOR: UPPER LIP | 3C AT EDGE, 3D WITH VEINS OF 72C AT BASE | 155D WITH VEINS OF 71A |
| LOWER LIP | 3C WITH AREA OF 9A WHERE LIP MEETS PALATE | 70D WITH STREAKS OF BETWEEN 2A & 2C |
| INSIDE THROAT | 155D WITH HAIRS OF 155D AND TWO SPOTS OF 4A AT BASE | 155D WITH HAIRS OF 155D AND VENATION OF 72B |

I claim:

1. A new and distinct cultivar of Antirrhinum plant named Balumyell substantially as herein shown and described, which:

(a) exhibits a trailing growth habit, (b) forms abundant bright purple and yellow flowers and (c) exhibits dark green foliage.

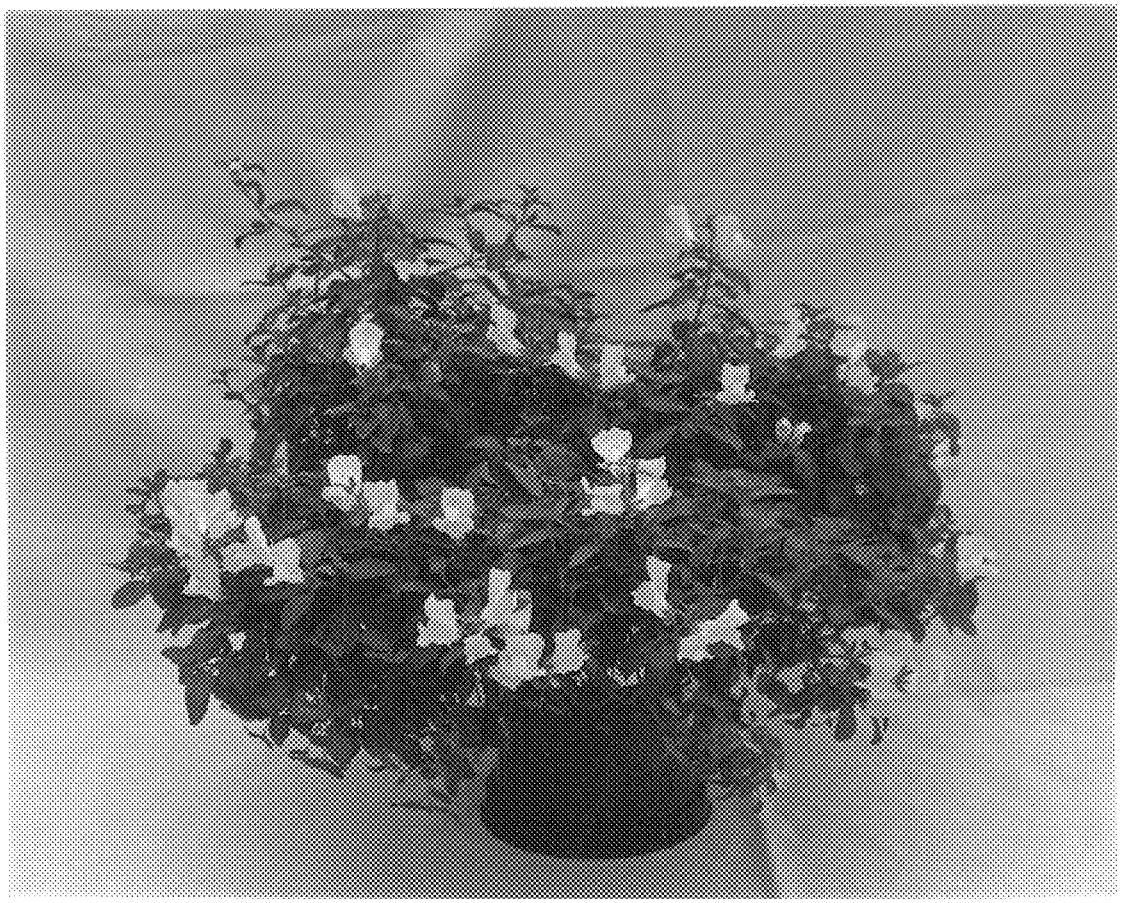

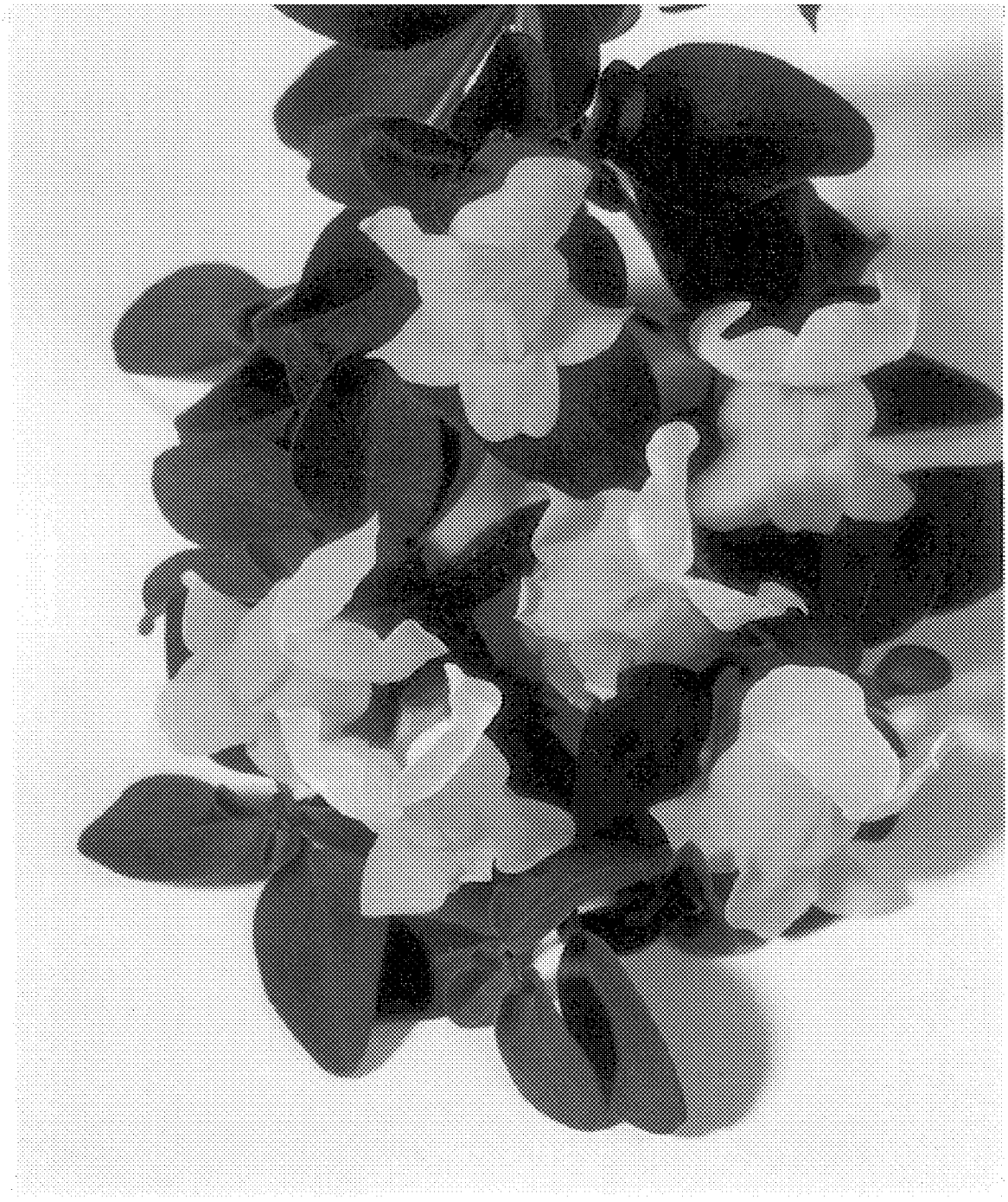

* * * * *